US008856993B2

(12) United States Patent
Richards et al.

(10) Patent No.: US 8,856,993 B2
(45) Date of Patent: Oct. 14, 2014

(54) TEMPERATURE AND MOISTURE REGULATING TOPPER FOR NON-POWERED PERSON-SUPPORT SURFACES

(75) Inventors: Sandy M. Richards, Pershing, IN (US); Sam M. Alsaeede, Indianapolis, IN (US); Andrew Kerr, Harrison, OH (US); Stephen C. Flint, Fortville, IN (US); Christopher R. O'Keefe, Batesville, IN (US); Charles A. Lachenbruch, Lakeway, TX (US)

(73) Assignee: Hill-Rom Services, Inc., Batesville, IN (US)

(*) Notice: Subject to any disclaimer, the term of this patent is extended or adjusted under 35 U.S.C. 154(b) by 565 days.

(21) Appl. No.: 13/099,543

(22) Filed: May 3, 2011

(65) Prior Publication Data

US 2011/0247143 A1 Oct. 13, 2011

Related U.S. Application Data

(63) Continuation-in-part of application No. 12/937,306, filed as application No. PCT/US2009/040661 on Apr. 15, 2009.

(60) Provisional application No. 61/045,111, filed on Apr. 15, 2008.

(51) Int. Cl.
| | |
|---|---|
| A47C 21/04 | (2006.01) |
| A47C 27/00 | (2006.01) |
| A47C 31/00 | (2006.01) |
| A47C 27/18 | (2006.01) |
| A47C 27/08 | (2006.01) |
| A61G 7/057 | (2006.01) |
| A61F 7/00 | (2006.01) |

(52) U.S. Cl.
CPC ..... *A47C 27/005* (2013.01); *A61G 2007/05792* (2013.01); *A61F 2007/0064* (2013.01); *A47C 31/006* (2013.01); *A47C 27/18* (2013.01); *A47C 27/088* (2013.01); *A61G 2210/90* (2013.01); *A61G 2210/70* (2013.01)
USPC .......... 5/726; 5/724; 5/423; 5/652.2

(58) Field of Classification Search
USPC ............... 5/421, 423, 652.1, 652.2, 724–726, 5/941, 699, 737, 738, 740, 655.9, 953, 5/727–729, 731, 734; 96/11
See application file for complete search history.

(56) References Cited

U.S. PATENT DOCUMENTS

| | | | | |
|---|---|---|---|---|
| 2,767,410 A | * | 10/1956 | Benson | 5/734 |
| 4,665,573 A | * | 5/1987 | Fiore | 5/731 |

(Continued)

FOREIGN PATENT DOCUMENTS

| | | |
|---|---|---|
| CA | 2411539 C | 9/2008 |
| EP | 2298264 A2 | 3/2011 |

(Continued)

OTHER PUBLICATIONS

CareSelections by Hill-Rom; Wound Care Therapy Products; Brochure; 132952; Mar. 4, 2005.

(Continued)

*Primary Examiner* — Robert G Santos
(74) *Attorney, Agent, or Firm* — Jason Penninger

(57) ABSTRACT

A person-support surface comprises a non powered mattress and a coverlet positionable on the non powered mattress. The coverlet includes an entry positioned at a first end of the coverlet, an exit positioned at a second end of the coverlet opposite the entry, an upper air impermeable layer, and a lower air impermeable layer coupled to the upper air impermeable layer to form an air flow path along the coverlet between the entry and the exit. The upper air impermeable layer is a vapor permeable and the lower air impermeable layer is a vapor permeable.

20 Claims, 8 Drawing Sheets

(56) References Cited

U.S. PATENT DOCUMENTS

| | | | |
|---|---|---|---|
| 5,048,137 A * | 9/1991 | Rogers | 5/731 |
| 5,687,438 A | 11/1997 | Biggie et al. | |
| 5,800,480 A | 9/1998 | Augustine et al. | |
| 5,882,349 A | 3/1999 | Wilkerson et al. | |
| 6,197,045 B1 | 3/2001 | Carson | |
| 6,421,859 B1 | 7/2002 | Hicks et al. | |
| 6,442,780 B1 * | 9/2002 | Phillips et al. | 5/730 |
| 6,730,115 B1 * | 5/2004 | Heaton | 607/104 |
| 6,782,574 B2 * | 8/2004 | Totton et al. | 5/713 |
| 6,855,158 B2 | 2/2005 | Stolpmann | |
| 6,874,185 B1 * | 4/2005 | Phillips et al. | 5/730 |
| 7,296,315 B2 | 11/2007 | Totton et al. | |
| 7,469,436 B2 * | 12/2008 | Meyer et al. | 5/727 |
| 7,480,953 B2 | 1/2009 | Romano et al. | |
| 7,641,623 B2 | 1/2010 | Biondo et al. | |
| 7,657,956 B2 * | 2/2010 | Stacy et al. | 5/713 |
| 7,914,611 B2 * | 3/2011 | Vrzalik et al. | 96/11 |
| 7,937,791 B2 * | 5/2011 | Meyer et al. | 5/727 |
| 7,975,335 B2 * | 7/2011 | O'Keefe et al. | 5/616 |
| 8,006,333 B2 * | 8/2011 | Genaro et al. | 5/615 |
| 8,118,920 B2 * | 2/2012 | Vrzalik et al. | 96/11 |
| 8,196,240 B2 * | 6/2012 | Meyer et al. | 5/727 |
| 8,196,241 B2 * | 6/2012 | Balonick et al. | 5/740 |
| 8,201,292 B2 * | 6/2012 | Dionne et al. | 5/713 |
| 8,372,182 B2 * | 2/2013 | Vrzalik et al. | 96/11 |
| 8,474,074 B2 * | 7/2013 | O'Keefe et al. | 5/616 |
| 8,531,307 B2 * | 9/2013 | Lachenbruch | 340/665 |
| 2002/0073489 A1 * | 6/2002 | Totton et al. | 5/713 |
| 2003/0145380 A1 | 8/2003 | Schmid | |
| 2005/0273941 A1 | 12/2005 | Stolpmann et al. | |
| 2006/0168736 A1 * | 8/2006 | Meyer et al. | 5/727 |
| 2007/0056101 A1 | 3/2007 | Mahajan et al. | |
| 2007/0261548 A1 * | 11/2007 | Vrzalik et al. | 95/52 |
| 2007/0266499 A1 * | 11/2007 | O'Keefe et al. | 5/713 |
| 2008/0028533 A1 * | 2/2008 | Stacy et al. | 5/713 |
| 2008/0047325 A1 | 2/2008 | Bartlett | |
| 2008/0120780 A1 * | 5/2008 | Genaro et al. | 5/600 |
| 2008/0141463 A1 * | 6/2008 | Dionne et al. | 5/713 |
| 2008/0263776 A1 | 10/2008 | O'Reagan et al. | |
| 2009/0000031 A1 | 1/2009 | Feher | |
| 2009/0119846 A1 * | 5/2009 | Meyer et al. | 5/709 |
| 2009/0217460 A1 * | 9/2009 | Bobey et al. | 5/709 |
| 2009/0222996 A1 * | 9/2009 | Balonick et al. | 5/730 |
| 2010/0122417 A1 * | 5/2010 | Vrzalik et al. | 5/652.1 |
| 2010/0132116 A1 * | 6/2010 | Stacy et al. | 5/423 |
| 2010/0274331 A1 * | 10/2010 | Williamson et al. | 607/104 |
| 2011/0024076 A1 * | 2/2011 | Lachenbruch et al. | 165/11.1 |
| 2011/0068939 A1 * | 3/2011 | Lachenbruch | 340/626 |
| 2011/0209289 A1 * | 9/2011 | Meyer et al. | 5/699 |
| 2011/0219548 A1 * | 9/2011 | Vrzalik et al. | 5/699 |
| 2011/0247143 A1 * | 10/2011 | Richards et al. | 5/713 |
| 2011/0258780 A1 * | 10/2011 | O'Keefe et al. | 5/618 |
| 2012/0012277 A1 * | 1/2012 | Lachenbruch | 165/60 |
| 2012/0144584 A1 * | 6/2012 | Vrzalik et al. | 5/600 |
| 2013/0074272 A1 * | 3/2013 | Lachenbruch et al. | 5/691 |
| 2013/0081205 A1 * | 4/2013 | Frondorf et al. | 5/613 |
| 2014/0007346 A1 * | 1/2014 | Lachenbruch | 5/421 |
| 2014/0068869 A1 * | 3/2014 | Lafleche et al. | 5/724 |

FOREIGN PATENT DOCUMENTS

| | | |
|---|---|---|
| WO | 9747268 A1 | 12/1997 |
| WO | 2009129306 A1 | 10/2009 |

OTHER PUBLICATIONS

Hill-Rom Advanced Surface Technology; Advanced Surface Technology for Positive Patient Outcomes; Brochure; Nov. 9, 2007.

The Joint Commission Journal on Quality and Patient Safety; Eliminating Facility-Acquired Pressure Ulcers at Ascension Health; Wanda Gibbons, R.N., H.H.A.; Helana T. Shanks, R.N.; Pam Kleinhelter, R.N., M.S.N.; Polly Jones, L.C.S.W.; Joint Commission on Accreditation of Healthcare Organizations, Oakbrook Terrace, IL 60181; Sep. 2006, vol. 32 No. 9.

European Search Report for EP Application 12166447.8; Place of Search—Munich; Date of completion of the search—Jul. 17, 2013.

* cited by examiner

TEMPERATURE AND MOISTURE REGULATING TOPPER FOR NON-POWERED PERSON-SUPPORT SURFACES

This application is a continuation-in-part U.S. patent application Ser. No. 12/937,306 filed on Oct. 11, 2010, which is a US National Application of International Application Serial No. PCT/US2009040661 filed under 37 C.F.R. § 371(b) on Apr. 15, 2009, which claims priority to U.S. Provisional Application Ser. No. 61/045,111 filed on Apr. 15, 2008, the contents of which are hereby incorporated by reference.

BACKGROUND OF THE DISCLOSURE

This disclosure relates generally to person support surfaces. More particularly, but not exclusively, one illustrative embodiment relates to person-support surfaces including a non-powered mattress with temperature and moisture regulating topper coupled thereto.

Patients lying on non-powered person support surfaces for extended periods of time can be susceptible to the development of pressure ulcers. While various non-powered person-support surfaces have been developed, there is still room for improvement. Thus, a need persists for further contributions in this area of technology.

SUMMARY OF THE DISCLOSURE

One illustrative embodiment of the present disclosure includes a person support surface with a non-powered mattress and a coverlet coupled to the non-powered mattress having a vapor permeable and air impermeable person contacting surface and mattress contacting surface configured to exhaust heat and moisture communicated through the person contacting surface out an outlet in the coverlet. Another illustrative embodiment includes a fluid supply assembly with conduit and a fluid supply configured to be activated/deactivated when the conduit is coupled to a person-support surface.

Additional features alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

Referring now to the illustrative examples in the drawings, wherein like numerals represent the same or similar elements throughout.

DETAILED DESCRIPTION OF THE DRAWINGS

Figure 1:
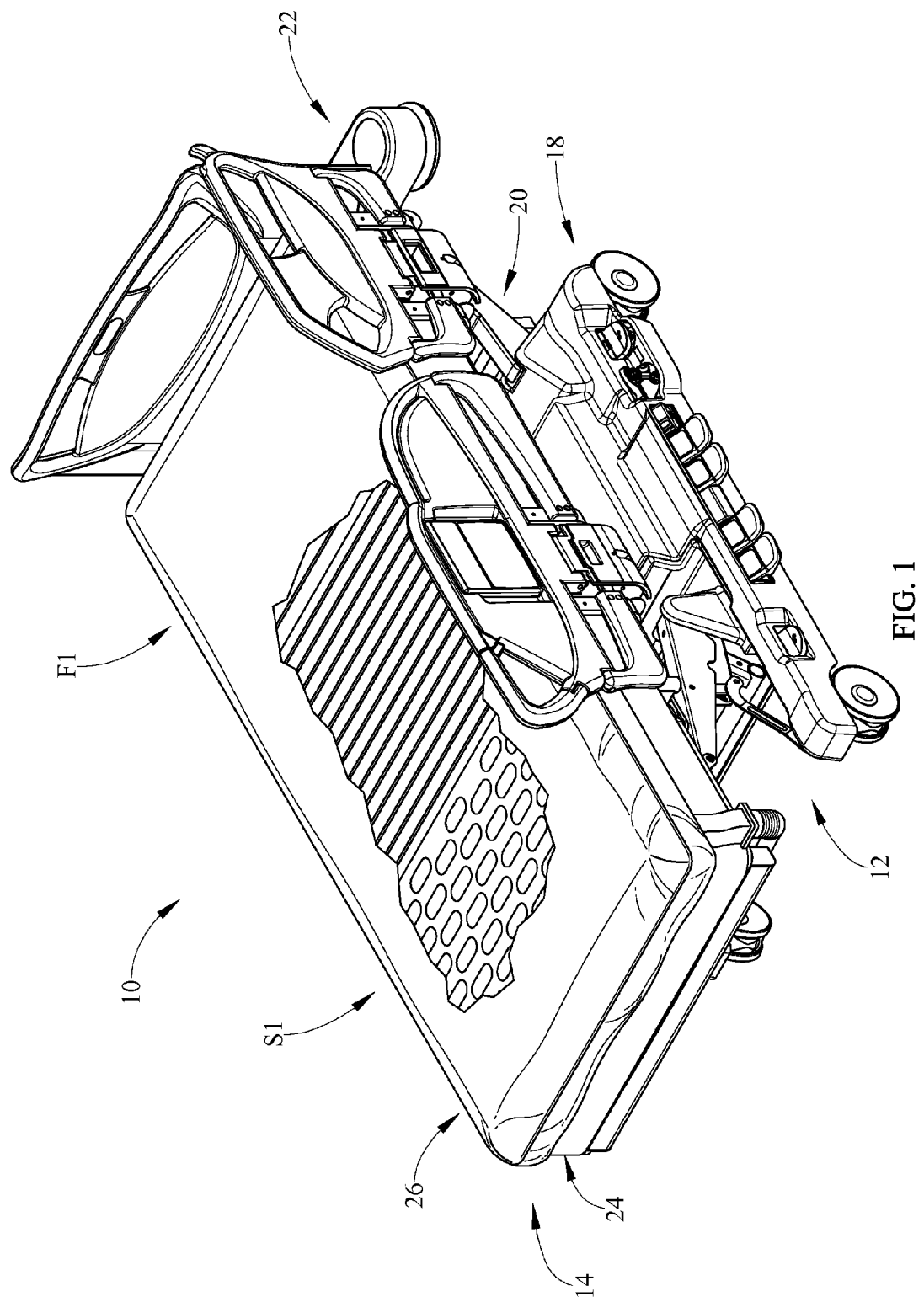
FIG. 1 is a perspective side view of a person-support system with a person-support surface supported on a person-support apparatus and a fluid supply assembly in fluid communication with the person-support surface.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

One illustrative embodiment of the present disclosure includes a person support surface with a non-powered mattress and a coverlet coupled to the non-powered mattress having a vapor permeable and air impermeable person contacting surface and mattress contacting surface configured to exhaust heat and moisture communicated through the person contacting surface out an outlet in the coverlet. Another illustrative embodiment includes a fluid supply assembly with conduit and a fluid supply configured to be activated/deactivated when the conduit is coupled to a person-support surface.

A person-support system 10 according to one illustrative embodiment of the current disclosure is shown in FIGS. 1-8. The person-support system 10 includes person-support apparatus 12, a person-support surface 14 supported on the person-support apparatus 12, and a fluid supply assembly 16 in communication with the person-support surface 14. In one illustrative embodiment, the fluid supply assembly 16 and the person-support surface 14 are part of a mattress replacement system.

The person-support apparatus 12 includes a lower frame 18, supports 20 or lift mechanisms 20 coupled to the lower frame 18, and an upper frame 22 movably supported above the lower frame 18 by the supports 20 as shown in FIG. 1. In one illustrative embodiment, the person-support apparatus 12 is a hospital bed frame with a first section F1 or head support section F1, where the head of a person (not shown) can be positioned and a second section S1 or a foot support section S1, where the feet of the person (not shown) can be positioned. The person-support apparatus 12 can also be a stretcher, an operating room table, a wheel chair, or other person supporting structure.

Figure 2:
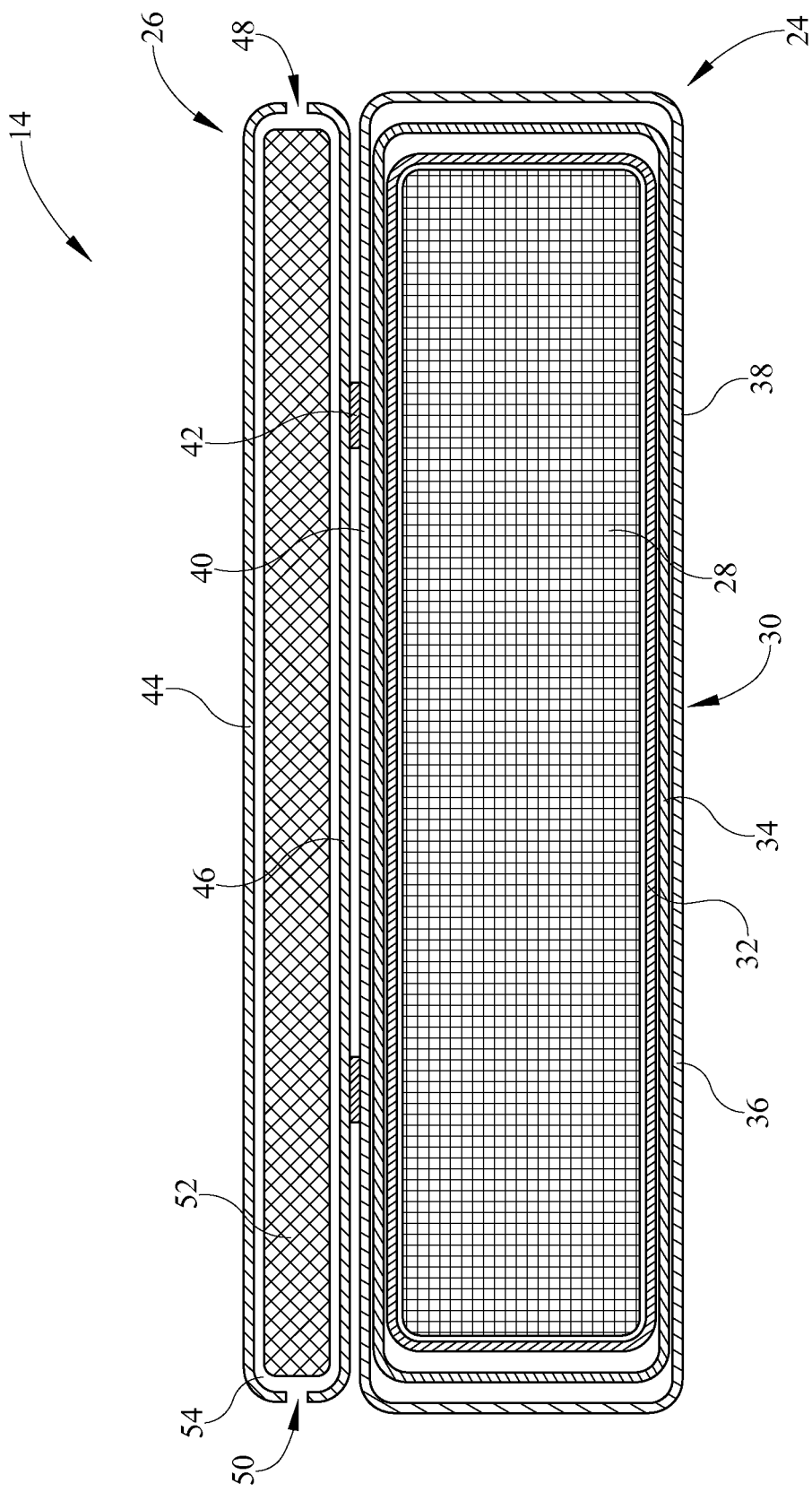
FIG. 2 is a side cross-sectional view of the person support surface of FIG. 1 showing the components of the non-powered mattress and the coverlet.
Figure 3:
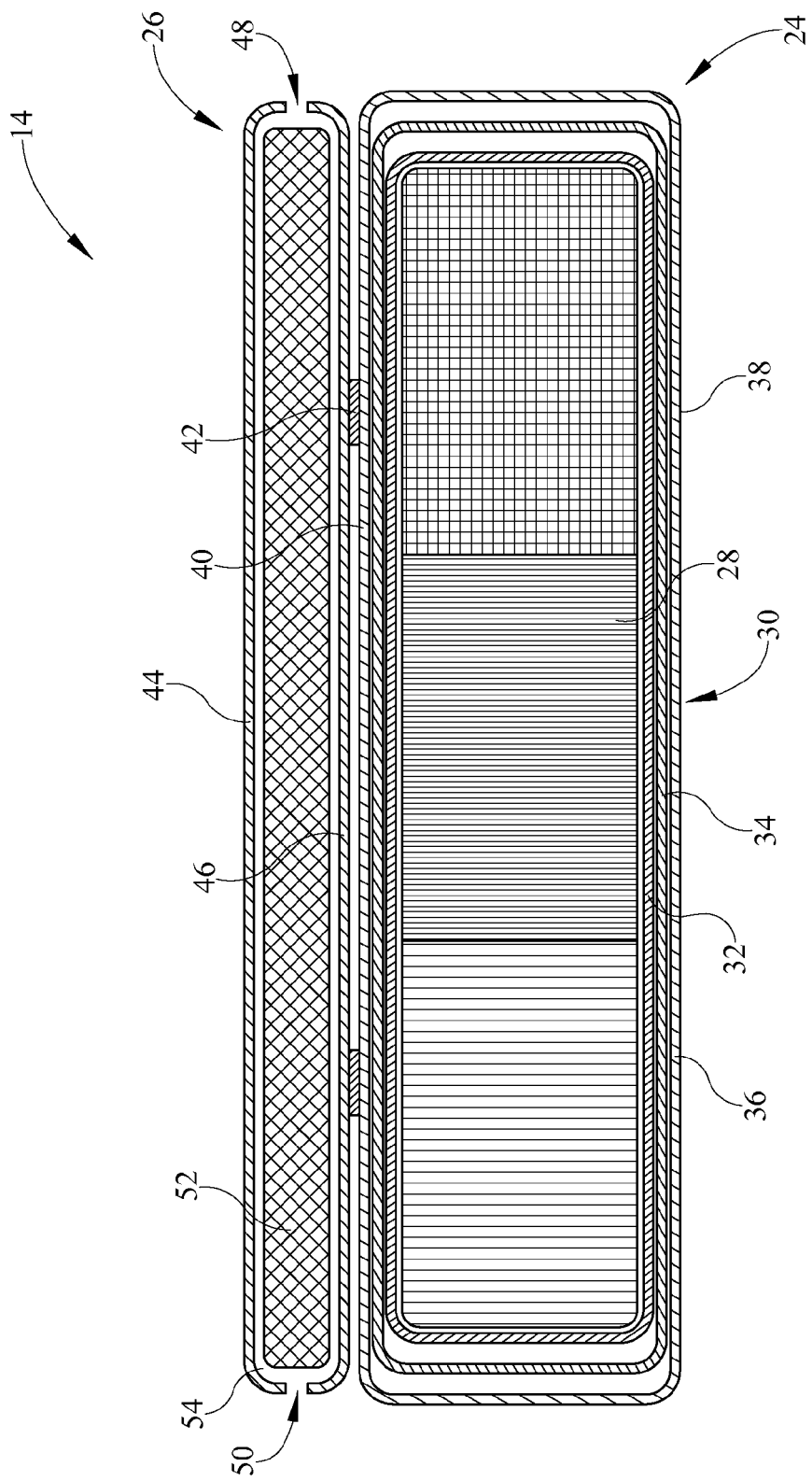
FIG. 3 is a side cross-sectional view of the person support surface of FIG. 1 showing the core of the non-powered mattress having varying support characteristics.
Figure 4:
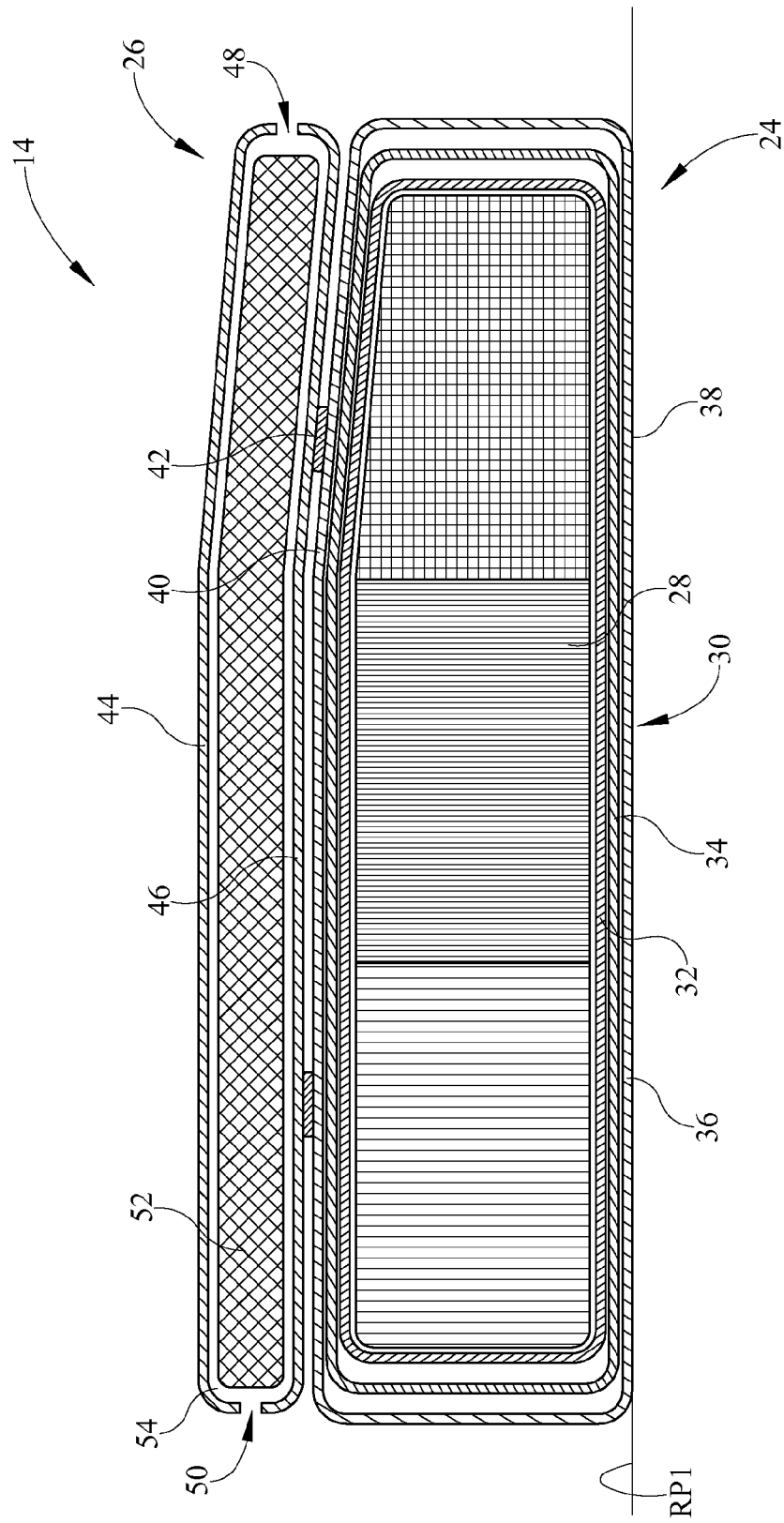
FIG. 4 is a side cross-sectional view of the person-support surface of FIG. 1 having a sloped foot section according to one illustrative embodiment.
Figure 5:
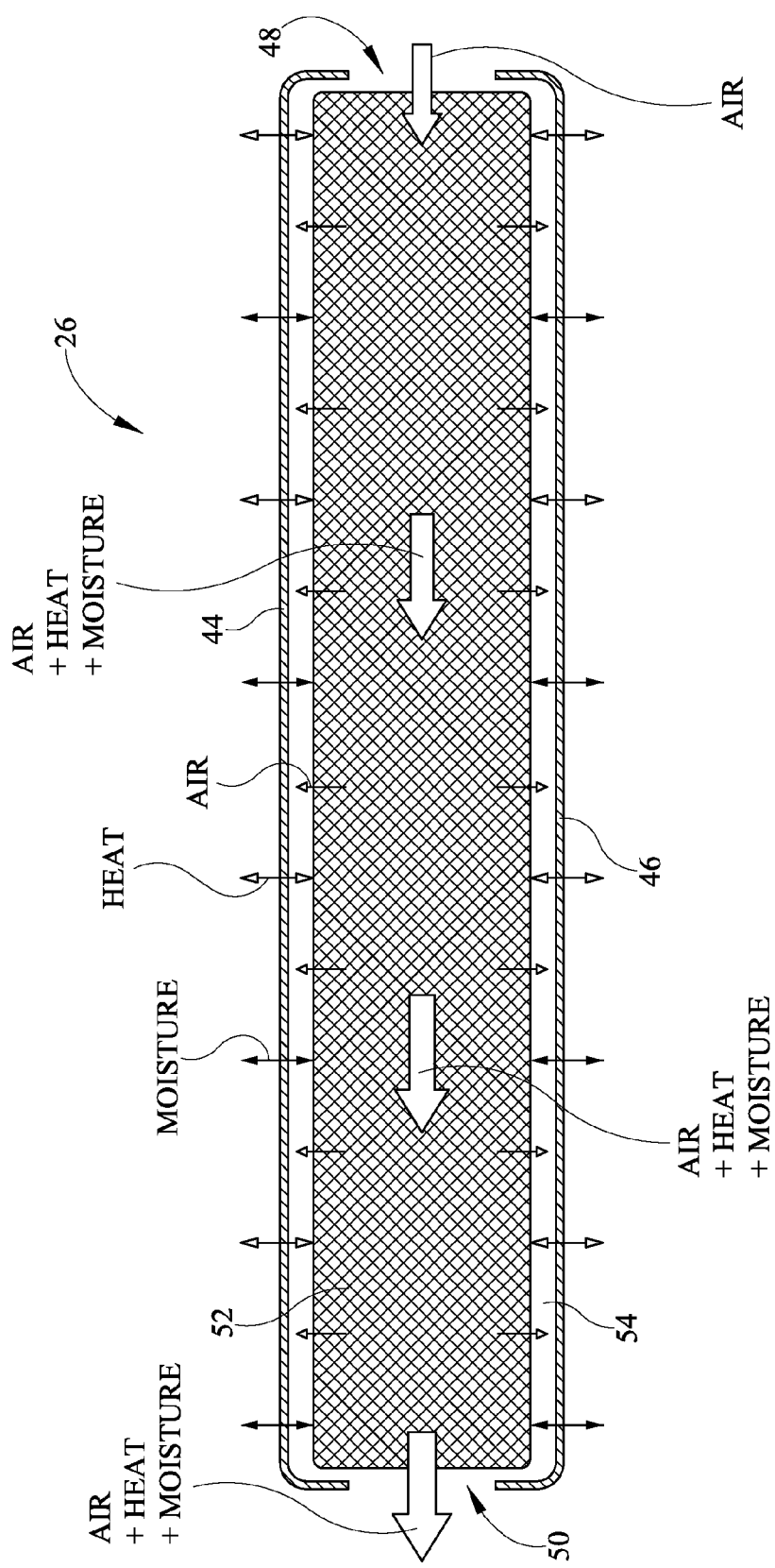
FIG. 5 is a side cross-sectional view of the coverlet of FIG. 1 showing the communication of heat and moisture through the top and bottom layers of the coverlet and the flow of air thorough the coverlet.

The person-support surface 14 includes a non-powered mattress 24 and a coverlet 26 positioned on the mattress 24 as shown in FIGS. 1-4. The non-powered mattress 24 includes a mattress core 28 and a mattress cover 30. In one illustrative embodiment, the non-powered mattress 24 is or is similar to at least one of the following mattresses sold by Hill-Rom® at 1069 State Route 46 East in Batesville, Ind.: the NP50 Prevention Surface, the NP100 Prevention Surface, the Tempur-Pedic® Mattress, the AccuMax Quantum™ VPC Therapy Surface, and/or the NP200 Wound Surface. In another illustrative embodiment, the foot section S1 of the non-powered mattress 24 includes a slight gradient to help reduce interface pressure on a person's heel. In one example, the foot section S1 of the non-powered mattress 24 is negatively sloped with respect to a reference plane RP1 as shown in FIG. 4.

The mattress core 28 can be composed of a single type of material or a combination of materials and/or devices. In one illustrative embodiment, the mattress core 28 is composed of single density foam as shown in FIG. 2. In another illustrative embodiment, the mattress core 28 includes multiple zones of high-density foam configured to enhance pressure redistribution as a function of a person's body's proportional differences as shown in FIGS. 1 and 3-4. In yet another illustrative embodiment, the mattress core 28 can include static air bladders and/or static air bladders with foam contained therewithin.

The cover 30 can enclose the mattress core 28 and includes a fire barrier 32, a bottom ticking 34 or durable layer 34, and a top ticking 36 as shown in FIGS. 2-4. In one illustrative embodiment, the fire barrier 32 is the innermost layer of the cover 30, the top ticking 36 is the outermost layer, and the bottom ticking 34 is positioned between the fire barrier 32 and the top ticking 36 and is not coupled to the top ticking 36. The bottom ticking 34 and the top ticking 36 are vapor and air impermeable. In one illustrative embodiment, the top ticking 36 and the bottom ticking 34 are composed of polyurethane coated nylon and the bottom ticking 34 is configured to facilitate movement of the top ticking 36 with respect to the fire barrier 32.

The top ticking 36 includes a person-support apparatus engaging surface 38 with a person-support apparatus coupler (not shown), and a coverlet contacting surface 40 with a coverlet coupler 42 as shown in FIGS. 2-4. In one illustrative embodiment, the coverlet coupler 42 is a zipper and the person-support apparatus coupler is a hook and loop fastener with one portion coupled to the person-support apparatus 12 and the other coupled to the coverlet 26. In other embodiments, the coverlet coupler 42 can be a hook and loop fastener, snaps, and/or buttons. In still other embodiments, the coverlet coupler 42 can be elastic loops configured to engage the corners of the mattress 12.

The coverlet 26 is configured to regulate the amount of heat and moisture present on the surface of the coverlet 26 by flowing a fluid through the coverlet 26. The coverlet 26 includes a top layer 44, a bottom layer 46, an inlet 48, an outlet 50, and a 3-dimensionally engineered spacer 52 as shown in FIGS. 2-5. The top layer 44 and the bottom layer 46 are coupled together along their edges to form an inner chamber 54 therebetween. In one illustrative embodiment, the edges of the top layer 44 and the bottom layer 46 are coupled together using RF welding technology. The top layer 44 and the bottom layer 46 are both configured to be vapor permeable and air impermeable. This configuration prevents air passing through the coverlet 26 from impinging on the skin of a person positioned on the coverlet 26 while allowing the moisture produced by the person to pass through the top layer 44 and be exhausted with the air passing through the coverlet 26 out the outlet 50.

The 3-dimensionally engineered spacer 52 is positioned in the inner chamber 54 and is configured to be air and moisture permeable as shown in FIGS. 2-5. The 3-dimensionally engineered spacer 52 is configured to maintain a path for the air to flow through when a person is supported on the coverlet 26. In one illustrative embodiment, the 3-dimensionally engineered spacer 52 is Spacenet®.

The inlet 48 and the outlet 50 are generally located on opposite ends of the coverlet 26 and allow a fluid, such as, air, to be communicated into the inner chamber 54 of the coverlet 26, and to be exhausted from the coverlet 26, respectively, as shown in FIGS. 2-5. In one illustrative embodiment, the inlet 48 is located along the second section S1 of the coverlet 26 and the outlet 50 is located along the first section F1 of the coverlet 26. The inlet 48 includes an inlet connector 56 configured to couple to and receive fluid from the fluid supply assembly 16 as shown in FIG. 6.

The fluid supply assembly 16 is configured to cooperate with the coverlet 26 to regulate the amount of heat and moisture on at least a portion of the top layer 44 in contact, directly or indirectly, with the skin of a person supported on the person-support surface 14. Regulation of the heat and moisture levels can help prevent and/or heal undesirable skin conditions, such as, pressure ulcers. In one illustrative embodiment, the fluid supply 16 and coverlet 26 can cooperate to maintain at least one of a surface temperature, a relative surface humidity, and a heat withdrawal capacity of at least a portion of the surface which is in contact, directly or indirectly, with the person within a predefined range, for example, between about 90° F. and about 95.5° F.; between about 55% relative humidity and about 95% relative humidity; and/or between about 60 W/m$^2$ and about 125 W/m$^2$, as disclosed in, U.S. patent application Ser. No. 12/937,306, which is incorporated herein by reference.

Figure 6:
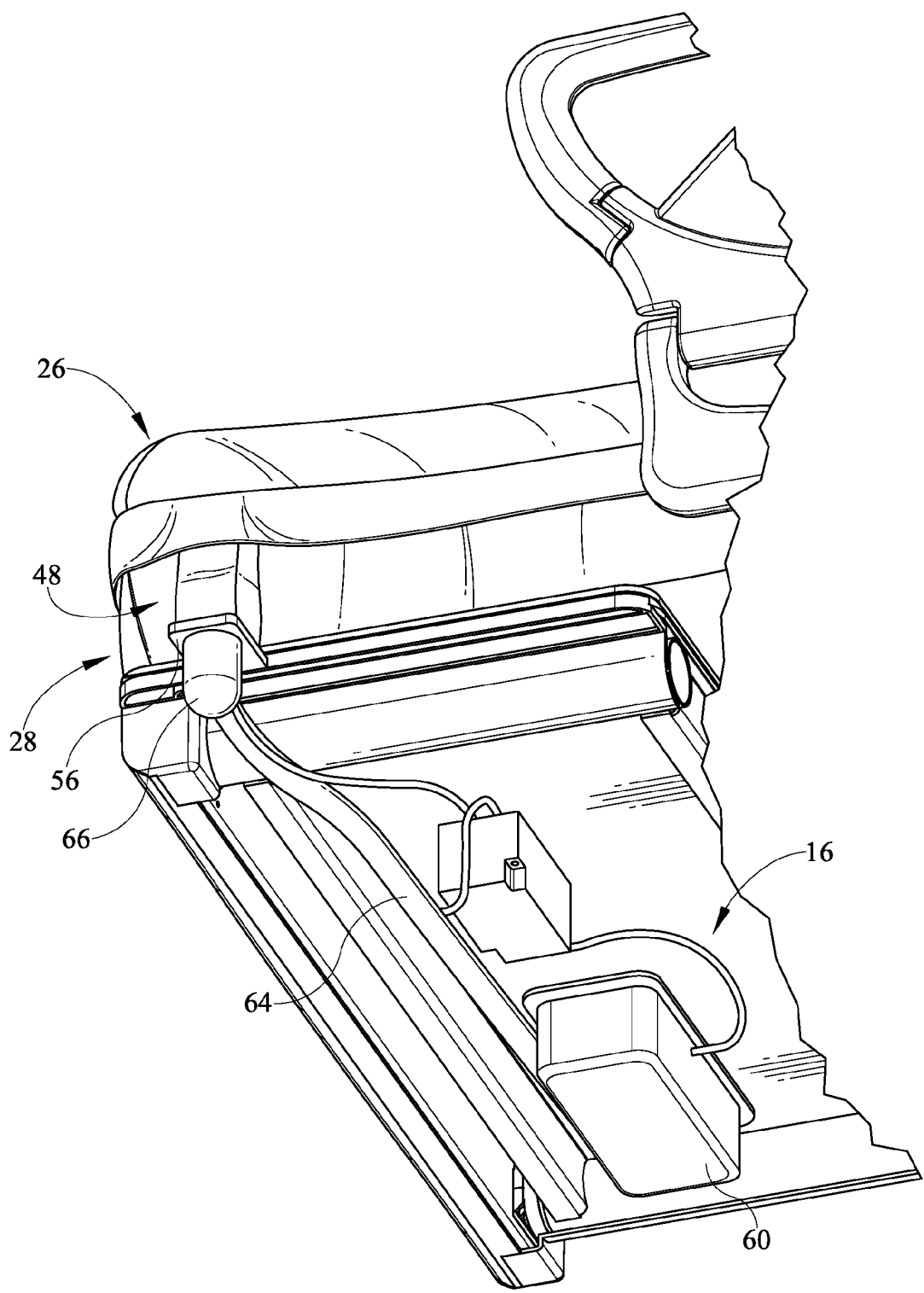
FIG. 6 is a perspective bottom view of the fluid supply assembly of FIG. 1 showing the conduit coupled to the coverlet, the fluid supply housing, and the controller.
Figure 7:
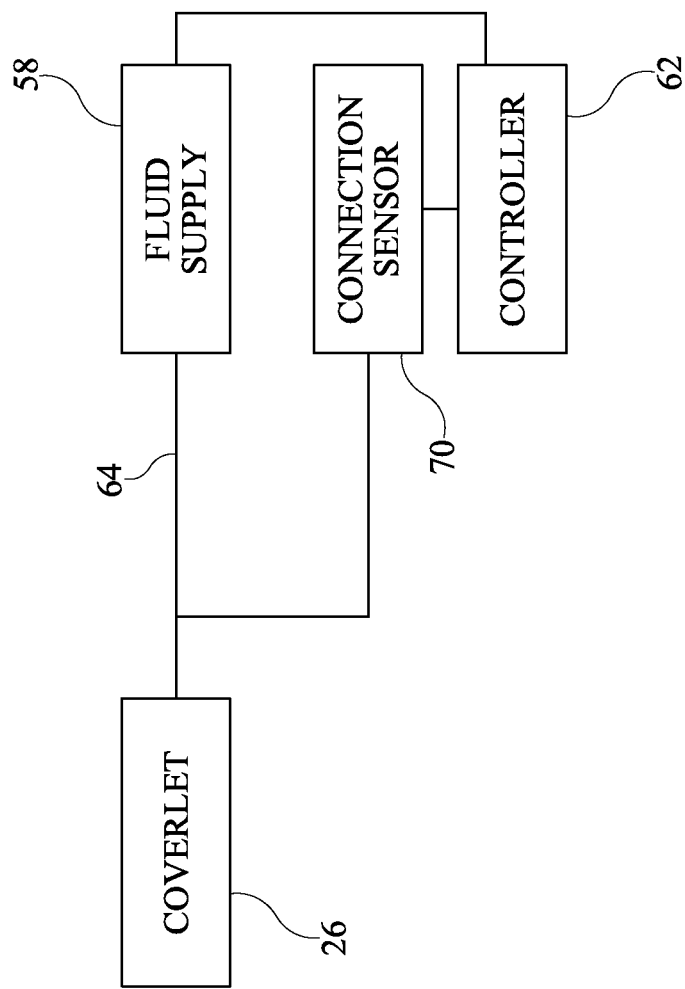
FIG. 7 is a block diagram of the fluid supply assembly of FIG. 6.
Figure 8:
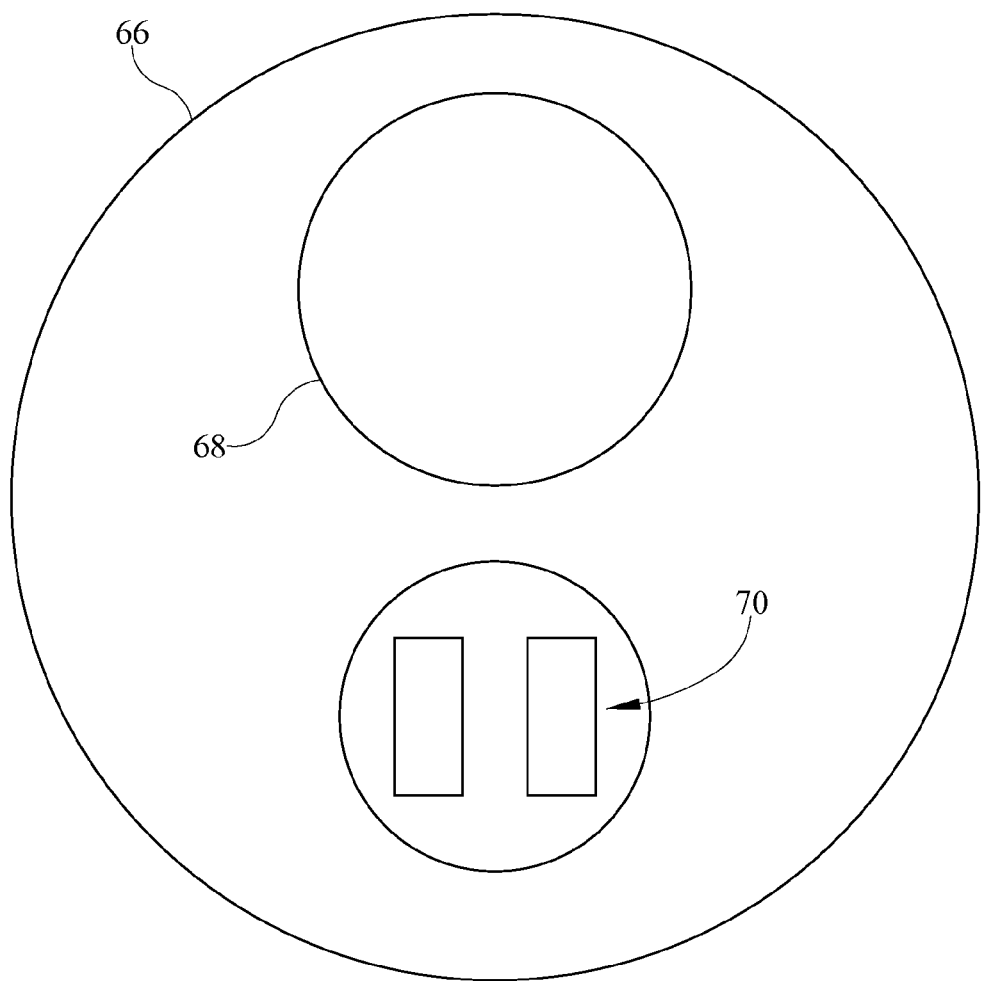
FIG. 8 is a front view of the conduit connector of the conduit of FIG. 6 showing the connection sensor.

The fluid supply assembly 16 includes a fluid supply 58 enclosed within a housing 60, a controller 62, and a conduit 64 as shown in FIGS. 6-8. In one illustrative embodiment, the fluid supply 58 is an air blower and the housing 60 is coupled to the underside of the second section S1 of the upper frame 22. In another illustrative embodiment, the housing 60 is integrated into a footboard (not shown) coupled to the person-support apparatus 12.

The controller 62 is configured to control the operation of the fluid supply 58. In one illustrative embodiment, the controller 62 activates and/or deactivates the fluid supply 58 when the conduit 64 is coupled/uncoupled to/from the coverlet 26. The controller 62 can also cause the fluid supply 58 to supply fluid at a predetermined rate and/or adjust the temperature and humidity of the fluid supplied by the fluid supply 58. In other illustrative embodiments, the controller 62 can activate/deactivate the fluid supply 58 when the conduit 64 is coupled/uncoupled to/from a therapy device, powered mattress, or other pneumatic device or instrument.

The conduit 64 is configured to facilitate communication of fluid between the fluid supply 58 and the coverlet 26 as shown in FIG. 6. In one illustrative embodiment, the conduit 64 is configured to be coupled to an outlet (not shown) of the fluid supply 58 and configured to be removably coupled to the inlet connector 56. The conduit 64 includes a conduit connector 66 with a fluid outlet port 68 and a connection sensor 70 as shown in FIG. 8. The connection sensor 70 is configured to sense when the conduit connector 66 is coupled to the inlet connector 56. In one illustrative embodiment, the connection sensor 70 is a pair of conductive strips configured to engage a conductive strip (not shown) on the inlet connector 56 that electrically connects the pair conductive strips to complete the circuit. This embodiment would not necessarily require a controller to activate/deactivate the fluid supply 58. In another illustrative embodiment, the sensor 70 is a switch (not shown).

In operation, the conduit connector 66 is not connected from the inlet connector 56. When a user desires for the temperature and moisture on the coverlet 26 to be regulated, the user connects the conduit connector 66 to the inlet connector 56. The connection sensor 70 senses when the conduit connector 66 and the inlet connector 56 are connected and the controller 62 activates the fluid supply 58. The fluid supply 58 communicates fluid through the conduit 64 to the inlet 48 of the coverlet 26. The fluid flows from the inlet 48 through the inner chamber 54 of the coverlet 26 and is exhausted out the outlet 50. As the fluid passes through the coverlet 26, heat and moisture communicated through the upper layer 44 and/or bottom layer 56 is absorbed by the fluid flow and exhausted with the fluid out the outlet 50.

Many other embodiments of the present disclosure are also envisioned. For example, a person-support surface comprises a non powered mattress and a coverlet positionable on the non powered mattress. The coverlet includes an entry positioned at a first end of the coverlet, an exit positioned at a second end of the coverlet, an upper air impermeable layer, and a lower air impermeable layer coupled to the upper air impermeable layer to form an air flow path along the coverlet between the entry and the exit. The upper air impermeable layer is a vapor permeable and water resistant fabric and the lower air impermeable layer is a vapor permeable and water resistant fabric.

In another example, a person-support surface comprises a non powered mattress, a topper, and an air supply. The non powered mattress includes a mattress core substantially enclosed within an air and vapor impermeable mattress cover. The topper is removably coupled to the non-powered mattress and includes an occupant interfacing surface and a non-powered mattress interfacing surface coupled together to define a chamber therebetween. The occupant interfacing surface and the non-powered mattress interfacing surface are vapor permeable and air impermeable. The topper has a first opening into the chamber along a first side and a second opening into the chamber along a second side. The air supply is in fluid communication with the topper through a conduit. The air enters the chamber through the first opening in the topper, flows through the chamber, and exits the chamber through the second opening. The air flow though the topper is configured to exhaust heat and moisture communicated into the chamber through the occupant interfacing surface out through the second opening.

In another example, a fluid supply system comprises a gas blower and a conduit coupled to the gas blower and configured to communicate gas therethrough. The conduit includes a connector configured to be removably coupled to a medical device. The gas blower is configured to be activated when the conduit is coupled to the medical device.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless can not be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and various combinations of inventive aspects and principles are possible in light of the various embodiments provided above.

What is claimed is:

1. A person-support system comprising:
 a non powered mattress; and
 a coverlet positionable on the non powered mattress and including
  an entry positioned at a first end of the coverlet,
  an exit positioned at a second end of the coverlet,
  an upper air impermeable layer, and
  a lower air impermeable layer coupled to the upper air impermeable layer to form an air flow path along the coverlet between the entry and the exit, wherein the upper air impermeable layer is vapor permeable, the lower air impermeable layer is vapor permeable.

2. The person-support system of claim 1 further comprising an air supply configured to provide air to the coverlet, the air supply and the coverlet cooperating to maintain at least one of a surface temperature, a relative humidity, and a heat withdrawal capacity of at least a portion of a surface of the coverlet within a predefined range.

3. The person-support system of claim 1, wherein the non powered mattress includes a mattress core and an air impermeable and vapor impermeable cover enclosing the mattress core.

4. The person-support system of claim 3, wherein the mattress core is composed of foam.

5. The person-support system of claim 1, wherein the non-powered mattress includes multiple zones, at least one of the zones is configured to have a different interface pressure characteristic than the other zones.

6. The person-support system of claim 1, wherein the non-powered mattress includes an array of gas filled bladders in fluid communication with each other, the gas filled bladders configured to communicate gas therebetween as a function of the pressure being applied to the array of gas filled bladders.

7. The person-support system of claim 6, wherein the gas filled bladders include foam positioned therein.

8. The person-support system of claim 1, wherein the non-powered mattress includes a foot section where an occupant's feet can be positioned, the foot section being negatively sloped with respect to a reference plane.

9. The person-support system of claim 1 further comprising a three dimensionally engineered spacer interposed between the upper and lower layers to facilitate air flow through the coverlet.

10. A person-support surface, comprising:
 a non powered mattress including a mattress core substantially enclosed within an air and vapor impermeable mattress cover; and
 a topper removably coupled to the non-powered mattress and including an occupant interfacing surface and a non-powered mattress interfacing surface coupled together to define a chamber therebetween, the occupant interfacing surface and the non-powered mattress interfacing surface being vapor permeable and air impermeable, the topper having a first opening into the chamber along one side of the enclosure and a second opening along another side of the enclosure; and a dedicated air supply in fluid communication with the topper through a conduit, the air entering the chamber though the first opening in the topper, flowing through the chamber, and exiting the chamber through the second opening, the air flow though the topper being configured to exhaust heat and moisture communicated into the chamber through the occupant interfacing surface out through the second opening, the dedicated air supply operable to maintain an operational characteristic of at least a portion of the mattress cover within a predefined range.

11. The person-support surface of claim 10, wherein the mattress core includes at least one air bladder.

12. The person-support surface of claim 10, wherein the mattress core is composed of foam.

13. The person-support surface of claim 10, wherein the conduit is removably couplable to at least one of the air supply and the topper, the air supply being activated when the conduit is connected to the air supply and the topper.

14. The person-support surface of claim 10, wherein the air supply is deactivated when the conduit is disconnected from at least one of the air supply and the topper.

15. The person-support system of claim 10, wherein the operational characteristic includes at least one of a surface temperature, a relative surface humidity, and a heat withdrawal capacity of the portion of the mattress cover.

16. A person-support system, comprising:
   a non powered mattress including a mattress core substantially enclosed within an air and vapor impermeable mattress cover; and
   a topper removably coupled to the non-powered mattress and including an occupant interfacing surface and a non-powered mattress interfacing surface coupled together to define a chamber therebetween, the occupant interfacing surface and the non-powered mattress interfacing surface being vapor permeable and air impermeable, the topper having a first opening into the chamber along one side of the enclosure and a second opening along another side of the enclosure;
   a fluid supply in fluid communication with the topper through a conduit, the fluid entering the chamber though the first opening in the topper, flowing through the chamber, and exiting the chamber through the second opening, the fluid flow though the topper being configured to exhaust heat and moisture communicated into the chamber through the occupant interfacing surface out through the second opening; and
   a control system configured to control the operation of the dedicated air supply to maintain at least one of a surface temperature, a relative surface humidity, and a heat withdrawal capacity of at least a portion of the mattress cover within a predefined range.

17. The person-support system of claim 16, wherein the mattress core is composed of foam.

18. The person-support system of claim 16, wherein the non-powered mattress includes multiple zones, at least one of the zones is configured to have a different interface pressure characteristic than the other zones.

19. The person-support system of claim 16, wherein the non-powered mattress includes a foot section where an occupant's feet can be positioned, the foot section being negatively sloped with respect to a reference plane.

20. The person-support system of claim 16 further comprising a three dimensionally engineered spacer interposed between the occupant interfacing surface and the non-powered mattress interfacing surface to facilitate air flow through the topper.

* * * * *